(12) United States Patent
Uttrachi

(10) Patent No.: US 8,104,094 B2
(45) Date of Patent: Jan. 31, 2012

(54) CLEAN, COOL, COMFORTABLE WELDING HELMET

(76) Inventor: Gerald Daniel Uttrachi, Florence, SC (US)

( * ) Notice: Subject to any disclaimer, the term of this patent is extended or adjusted under 35 U.S.C. 154(b) by 256 days.

(21) Appl. No.: 12/455,067

(22) Filed: May 29, 2009

(65) Prior Publication Data

US 2010/0299795 A1 Dec. 2, 2010

(51) Int. Cl.
*A61F 9/06* (2006.01)
(52) U.S. Cl. .............. 2/8.6; 2/7; 2/8.2; 2/8.3; 2/8.8
(58) Field of Classification Search ........... 2/8.6, 7, 2/8.1, 8.2, 171.3, 209.13, 905, 906, 422, 2/436; 128/201.22, 201.25, 863
See application file for complete search history.

(56) References Cited

U.S. PATENT DOCUMENTS

| 3,535,707 | A |   | 10/1970 | Greenlee |            |
|-----------|---|---|---------|----------|------------|
| 3,548,415 | A |   | 12/1970 | Walter   |            |
| 4,172,294 | A | * | 10/1979 | Harris   | 2/171.3    |
| 4,483,021 | A | * | 11/1984 | McCall   | 2/7        |
| 5,193,347 | A |   | 3/1993  | Apisdorf |            |
| 5,878,742 | A | * | 3/1999  | Figueredo et al. | 128/201.24 |
| 5,896,579 | A | * | 4/1999  | Johnson et al. | 2/8.6 |
| 6,070,264 | A | * | 6/2000  | Hamilton et al. | 2/8.8 |
| 6,829,784 | B2| * | 12/2004 | Austin   | 2/7 |
| 7,114,194 | B2| * | 10/2006 | English  | 2/171.3 |
| 7,296,304 | B2| * | 11/2007 | Goldsborough | 2/171.3 |
| 7,534,005 | B1|   | 5/2009  | Backman  |  |
| 2006/0283455 | A1| * | 12/2006 | Walker et al. | 128/206.24 |
| 2007/0056073 | A1|   | 3/2007  | Martin   |  |
| 2008/0073330 | A1| * | 3/2008  | Diedrick et al. | 219/133 |

* cited by examiner

*Primary Examiner* — Gary L Welch
*Assistant Examiner* — Andrew W Collins

(57) ABSTRACT

This invention defines a welding helmet that encloses a welders head on five sides and with an optional skirt covers their neck. The helmet contains a fan, filter and cooling module to provide clean cool air that reduces welding fume levels in the breathing zone below suggested maximums. By providing cool air to the welders head and neck area their whole body will feel cooler. It suggests the use of an external power source to provide the energy required to have a fan of sufficient capacity to draw air thorough a quality filter so potentially hazardous constituents of welding fumes are captured. This externally supplied power allows the required cooling capacity thermal electric cooling modules to be used to significantly lower the ambient air temperature. This helmet allows the welding operator to have sufficient cooling to improve their overall work environment for one of the most objectionable welding issues, excess heat.

5 Claims, 5 Drawing Sheets

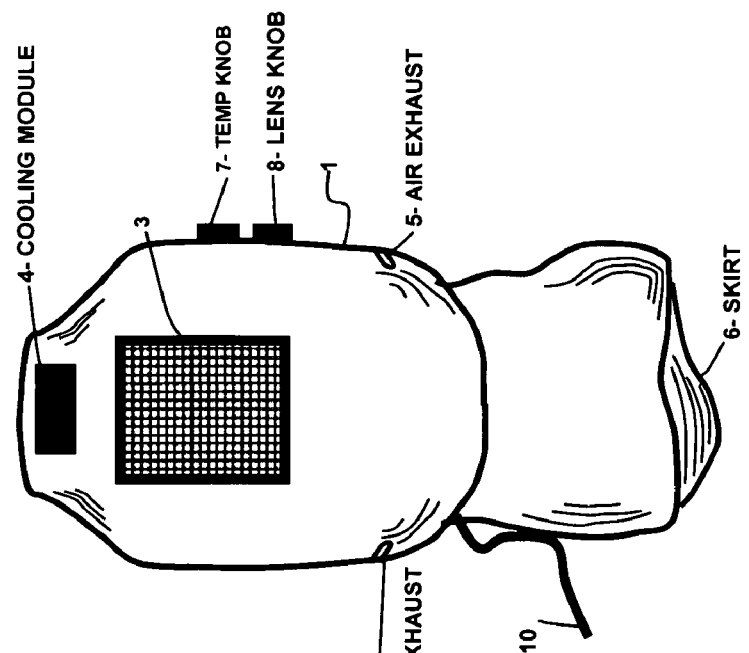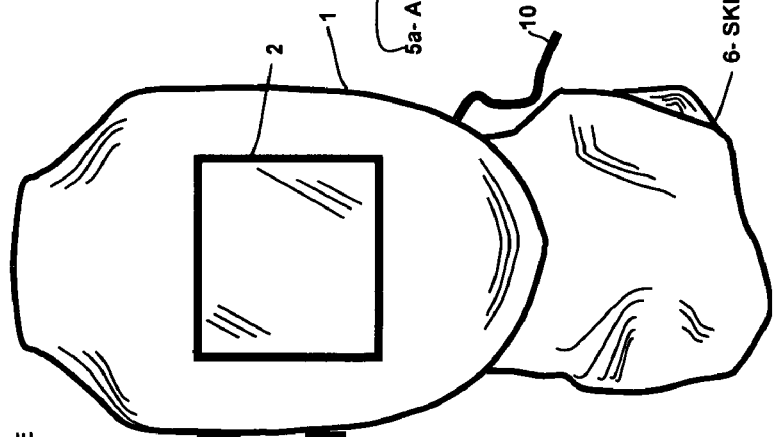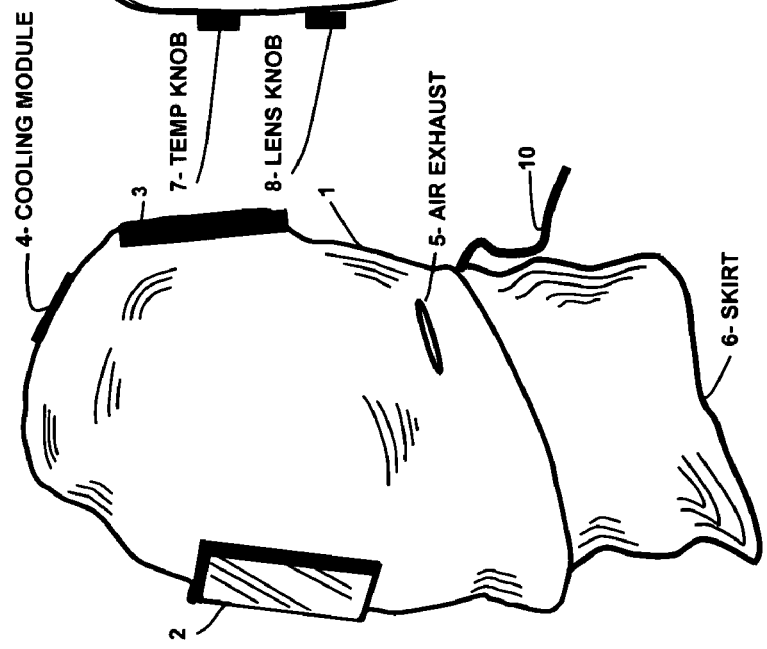

CLEAN, COOL, COMFORTABLE WELDING HELMET

BACKGROUND

1. Field of Invention

This invention is for a welding helmet that significantly reduces exposure to welding fumes, contains a mechanism to cool the air drawn into the helmet and assists with the overall comfort of the welding task.

2. Background

Welding is considered a hot and dirty occupation by many practitioners who work at the profession. Recently, allowable levels of specific fume constituents resulting from arc welding are at such low levels that conventional means of staying below these levels such as keeping the welders head out of the fume plume are not sufficient. For example the current maximum recommended fume exposure level for some chrome (VI) compounds is 0.01 mg/m.sup.3. Even employing source capture may not be sufficient to assure welder exposure levels are below that maximum. Some fume constituents in steel welding may exceed newly reduced fume constituent levels. This may require a welder to use a respirator which makes the hot working environment even more uncomfortable and objectionable. Considering a significant amount of welding occurring in shops which are not cooled in warm weather the use of devices such as respirators makes the welding occupation less attractive. When welding in very toxic environments air has been delivered to welding helmets from an external source through a long hose. This is not practical for most welding applications.

3. Description of Prior Art

There have been some welding helmets that attempt to address some of the problems encountered while welding:

(a) Walters U.S. Pat. No. 3,548,415 (1968) entitled "Air Conditioned Helmet" describes a device that incorporates a fan enclosed in an open helmet, not one used for welding. He discusses several means of creating cooling such as gels, heat pipes and mentions but does not elaborate on the possible use of a thermal electric principle. As with many of the devices reviewed, this one relies on battery power. It also does not mention any means of reducing welding fume levels to a very low level.

(b) Greenlee in U.S. Pat. No. 3,535,707 (1970) entitled "Welding Helmet and the Like," describes a welding helmet with a fan in the front which draws air from the rear of the helmet. The back of this helmet, as with most welding helmets, is open. At the very low allowable concentrations of some welding fume constituents this approach would not provide sufficiently low fume breathing air in most welding applications.

(c) Martin, et al in a US patent application 2007/0056073 entitled "Modular Auto-Darkening Welding Filter," discusses one of the optional features of the present invention, that of using external knobs to adjust some of the functions of the helmet. External adjustment of auto-darkening welding lens shade is common to some commercial welding helmets.

(d) Apisdorf in U.S. Pat. No. 5,193,317 (1993) entitled "Helmet-Mounted Air System for Personal Comfort," describes the use of a helmet that incorporates a thermal electric device to cool the air brought in by a fan. He discusses the small amount of cooling 0.4 to 4 degrees Centigrade the device provides and justifies it as being sufficient to cause comfort. Flow rates are also quite low, approximately 1 to 4 m³/minute. It appears he is justifying these low levels of flow and small amount of cooling to justify his device being powered by a battery placed on a belt.

(e) Buckman in U.S. Pat. No. 7,534,005 (2009) entitled "Welding Helmet," describes the use of multiple fans and a filter. However, the claims describe a conventional welding helmet with only front and sides, not the back or the top of the welders head covered. There is no mention of a cooling device of the thermal electric type or of any type that would significantly improve the welder's temperature environment.

SUMMARY, OBJECTS AND ADVANTAGES

It is the object of this present invention to incorporate a number of elements and features in a helmet design unique for the welding profession. These features provide an improved environment for the welder and cause welders to desire to use the device because of the improved working conditions.

The principle device employed is a unique type of welding helmet compared to what is used in the industry and that defined in prior art. A unique feature is the functional shape of the welding helmet. It has an external shape like an automotive racing helmet or a full face motorcycle helmet. That is, not only is it enclosed on the front and sides but also on the top and back. It is open on the bottom and worn like a racing helmet. However unlike a racing or motorcycle helmet it can be made from light weight materials only having to meet penetration tests to be certified by the American National Standards Institute. If desired it can be constructed to also meet the requirements for a "hard hat" where needed in construction, etc.

By employing an enclosed helmet it is possible to use a fan that pulls air through a quality replaceable filter designed to capture potentially harmful welding fume particles. The filter is placed at the back of the helmet where it is exposed to the least amount of welding fume. Air is channeled through an internal passageway on the top of the helmet above an adjustable head band. The head band provides for a custom fit for the wearer. A thermal electric cooling module(s) is placed in the air passageway. This cooling module operates on a principle defined by Jean Peltier in 1834. Solid state refrigerators and computer chip cooling devices use such devices. A thermal electric module has one surface that becomes cooler than ambient and the other that becomes hotter and can transfer heat to the external air. The location of this cooling module on the helmet surface allows the cold surface to be located in air passageway from the filter to an internal fan. The hot surface of the cooling module is placed outside the helmet and dissipates heat to the outside air. An electric motor powered fan is placed at the end of the air passageway and has a flow rate sufficient to pull air through a quality filter and force the filtered cooled air down over the wearers head. Some of the cool air will also flow over the welder's face. Studies have shown that head cooling reduces sweating in other parts of the body.

In certain welding applications to assure that welding fumes do not enter under the helmet an optional skirt is shown as part of this application. The skirt is made from a flexible, limited air permeability material and the top is fastened and sealed to the bottom open perimeter of the helmet. The skirt is of sufficient length so it can be tucked under a shirt or leather welding jacket. Properly designed it will not interfere with head movement.

The welding lens employed is of an auto-darkening type. When an arc is struck it switches from a clear lens to one darkened sufficiently to protect the wearer's eyes from the arc rays. It allows good vision when not welding and provides adequate blockage of arc rays when welding. It is possible to hinge the portion of the helmet containing the auto-darkening lens mechanism so it could be raised allowing the welder an opening directly to the outside. This requires a quality sealing system to avoid welding fumes entering around the lens. Since a number of viable mechanisms are available that would facilitate this possible embodiment, it is assumed one skilled in the art could implement this feature if desired and details are not covered in this patent application.

The power required to draw air into the helmet through a high efficiency filter and that required to power the thermal electric module(s) is more than could be obtained from a reasonable weight of batteries located in the helmet. Several unique characteristics of welding provide an opportunity to power the devices in the helmet with minimum connections and without long electrical lines, namely:

a) Arc welding requires a great deal of electrical power. The major welding process used in industry is referred to as MIG welding (Metal Inert Gas) or the official designation in the US is Gas Metal Arc Welding (GMAW.) The term MIG welding will be used for this patent application. MIG welding employs a continuously feed wire made of either steel, aluminum, stainless steel or other metal depending on the material being welded. For steel and stainless steel the wire can be solid or a product called cored wire where granular powder or flux ingredients are placed in the center of a tubular wire structure. All of these MIG welding processes utilize DC welding power ranging, for industrial systems, from 200 to 600 amperage capacity. Welding voltage typically ranges from 20 to 35 volts. It is possible to connect to this source to power the helmet with no ill effects on welding machine performance. Since welder safety is of paramount importance it is desirable to have the voltage going to the helmet to be less than about 24 volts. It is possible to reduce the welding voltage through appropriate circuitry and provide power at a safe voltage such as possibly 12 volts. Since the MIG welding torch is typically 15 feet in length, connecting the required DC power cord from the helmet to this low voltage DC source at the MIG wire feeder will require a minimum length power cord. With most MIG welders the DC voltage is not available when welding is stopped. It may be desirable to have the helmet powered between welds. Therefore, a large battery could be incorporated in the DC converter device. Since MIG wire feeders are generally somewhat bulky and heavy, often including 20 kg (44 pounds) or more of wire, the extra weight of a battery would normally not be a problem when placed at this location. The DC converter device could incorporate a system that charged the battery when welding.

b) Stick welding, another common arc welding process used in industry, provides an even easier method of powering the helmet. The formal designation for this process is Shielding Metal Arc Welding (SMAW.) Stick welding will be used in this application. In most instances, Stick welding power supplies are usually always energized with welding power whether an arc is struck or not. Therefore a converter to create the low voltage DC power can be relatively small and compact. Even if the Stick welding power is AC it can easily be converted to low voltage DC required for powering the helmet. The helmet power cord could be connected between the Stick power line coming from the power supply and the short length of power cable that comes with the Stick electrode holder. The cable supplying power to the helmet could be less than 3 meters (10 feet) long. The welding operator would connect their helmet power cord to the DC converter located where their Stick electrode holder connected to the Stick power line.

c) If desired, a power supply system could be used that is similar to that employed to power a laptop computer which also operate at low voltage DC. As with computer power supplies it could be plugged into any available AC power source. Many welding power supplies incorporate auxiliary AC power receptacles to power devices such as grinders.

d) A fourth alternative to power the helmet could be a backpack rechargeable battery.

There are several advantages of the proposed device over alternatives. To meet the increasingly lower maximum fume exposure levels, the use of quality respirators may be the only alternative choice for a number of applications. Respirators, even when used correctly, require a doctor to define if a worker is capable of breathing through these devices for an 8 hour day. Breathing through a respirator creates more stress on the heart. Some welders elect to have beards or mustaches. Facial hair is usually not allowed to properly fit a respirator. The heat involved with welding is often a complaint of operators. The potential to have a cooler work environment will offset the more confining helmet. The use of this helmet is a better alternative than using a conventional welding helmet and wearing a respirator.

Several additional benefits occur when having a fully enclosed welding helmet. The hot sparks from welding, called spatter, are prevented from hitting the top and back of the head causing burns. This is particularly an issue with current welding helmets when welding overhead or when other welders are in the immediate area. If the proposed helmet is combined with the optional skirt discussed, spatter hitting the skin on the neck is also eliminated.

DRAWING FIGURES

FIG. 3 is a left side view of the helmet with skirt.

FIG. 4 is a front view of the helmet and skirt also showing external knobs on the right side that adjusts auto-darkening shade and a temperature.

FIG. 5 is a view from the back of the helmet and optional skirt.

DESCRIPTION

Main Embodiment

Figure 1:
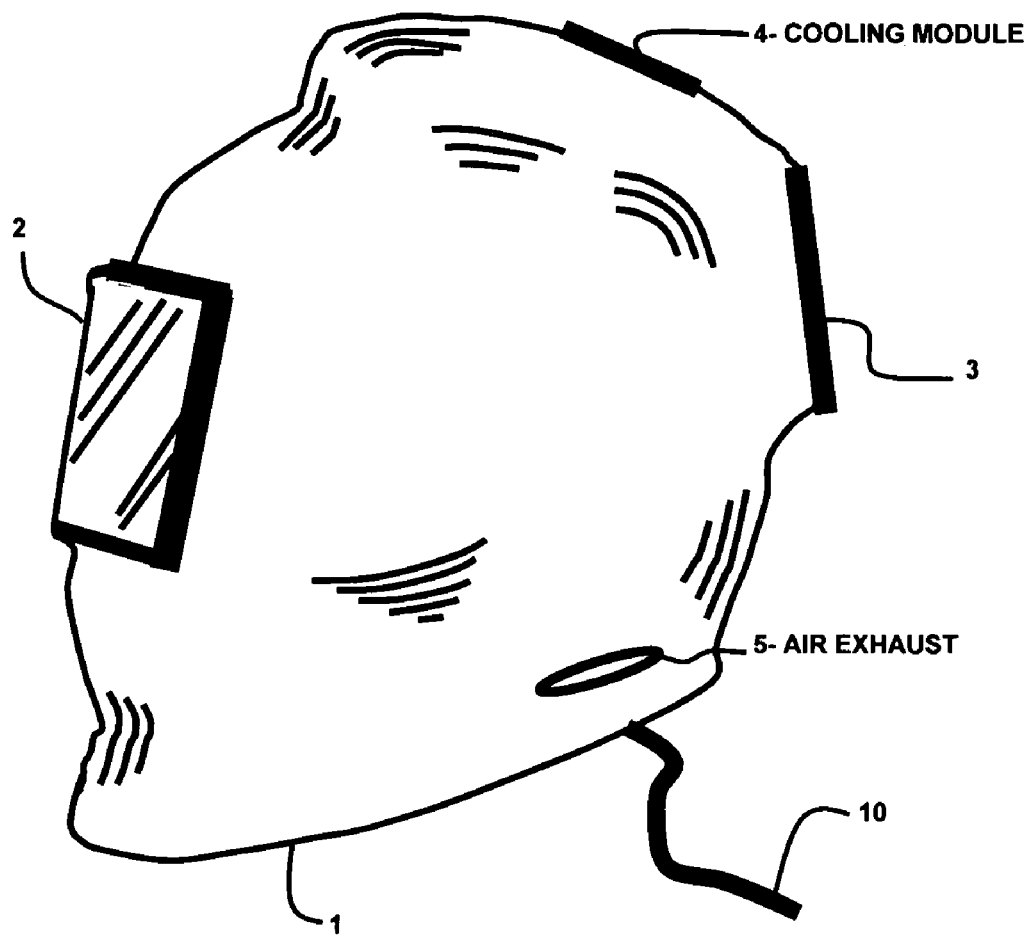
FIG. 1 shows a side view of the welding helmet with the filter and hot side of the thermal electric cooling module shown exposed at the top of the helmet.
Figure 2:
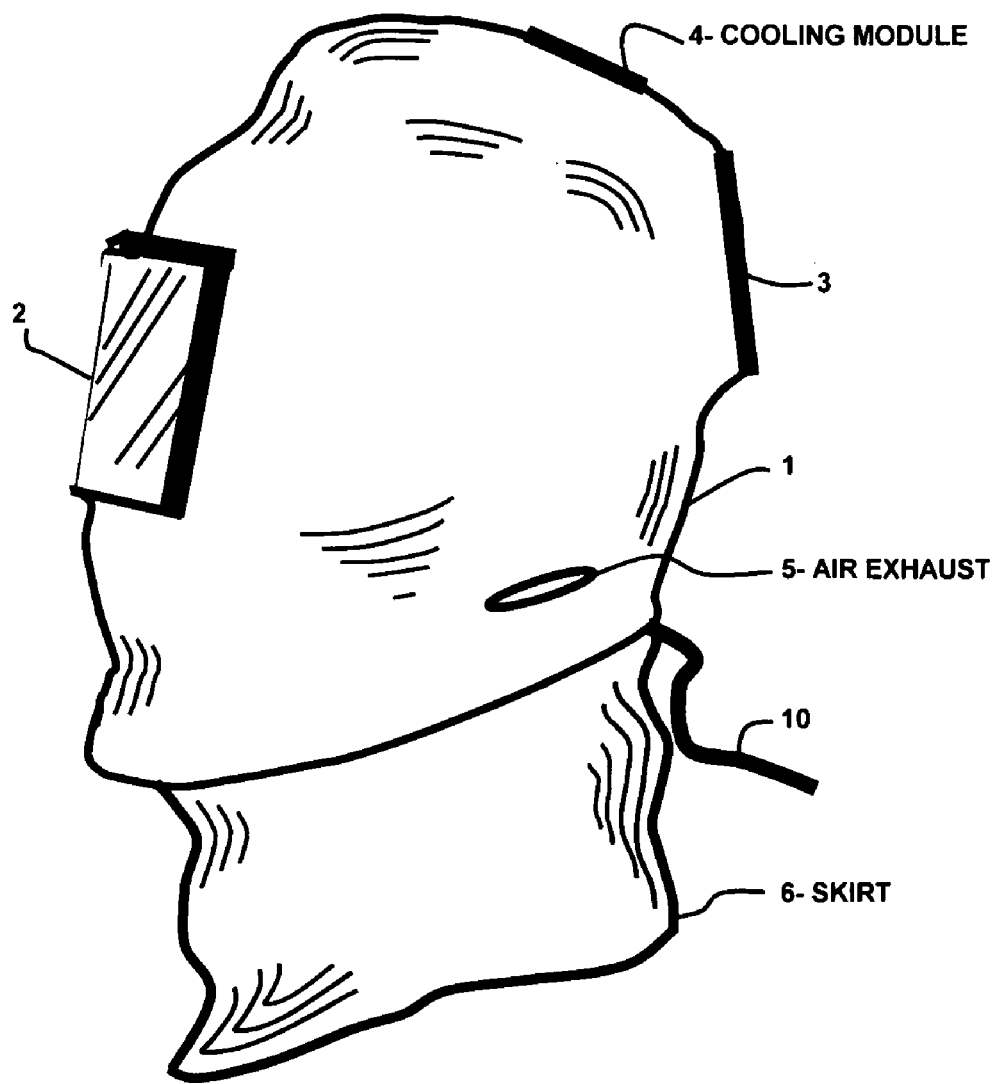
FIG. 2 shows the helmet with the optional skirt that reduces the possibility of welding fumes entering the bottom opening.

FIG. 1 illustrates the helmet 1 as viewed from the left side. The elements visible are the outer surface of helmet 1 that encloses the operators head in the front, right side, left side, top and back. A raised area is evident at the top of helmet 1. This raised area contains an internal air passageway 8 FIG. 6 that exists between a baffle 8*a* FIG. 6 and the top inner surface of helmet 1. Filter 3 is located at the inlet end of the air passageway 8 FIG. 6. The external hot side of thermal electric cooling module 4 is visible on the outside top of this raised area of helmet 1. A portion of the auto-darkening lens 2 is shown. Visible on this left side view is air exhaust 5 that is more functional when the optional skirt 6 FIG. 2 is used. Power cord 10 brings electrical power to helmet 1 from an external source (not shown).

FIG. 2 illustrates helmet 1 as viewed from the left side with the addition of skirt 6. Filter 3 and a portion of cooling module 4 are visible. A portion of the auto-darkening lens 2 is shown. Visible is air exhaust 5 that allows air to exit near the rear of the helmet 1. Air exhaust 5 could have baffles or even a one-way valve if needed in certain applications to avoid any external air from entering the helmet 1 without first going through the filter. This optional feature is not shown. Power cord 10 is also shown.

FIG. 3 is presented with two other figures, FIG. 4 and FIG. 5, to provide three different views of helmet 1 and skirt 6. Skirt 6 is made from non flammable material that can withstand being contacted with spatter and has limited air permeability to prevent air containing fumes from entering through the skirt. It is also important that skirt 6 be made from flexible material so as not to irritate or constrict the welder. The top of helmet 1 shows filter 3 and cooling module 4. An auto-darkening lens 2 is shown on the front with air exhaust 5. Power cord 10 is also shown.

FIG. 4 shows a front view of helmet 1 and skirt 6. Auto-darkening lens 2 is shown. It is possible to have the lens 2 hinged so the welding operator has access to the outside without removing helmet 1, that alternate configuration is not shown in this application as it could be incorporated in numerous ways. Temp knob 7 connects through the helmet 1 to control module 19 FIG. 6. It allows the welder to regulate the amount of cooling. Lens knob 8 is used to regulate the degree of lens 2 darkening. Power cord 10 is also shown.

FIG. 5 shows a rear view of helmet 1 and skirt 6. Filter 3 is shown. Temp knob 7 and lens knob 8 are visible. Both air exhaust 5 and air exhaust 5*a* are partially visible in this view. Power cord 10 is also shown.

Figure 6:
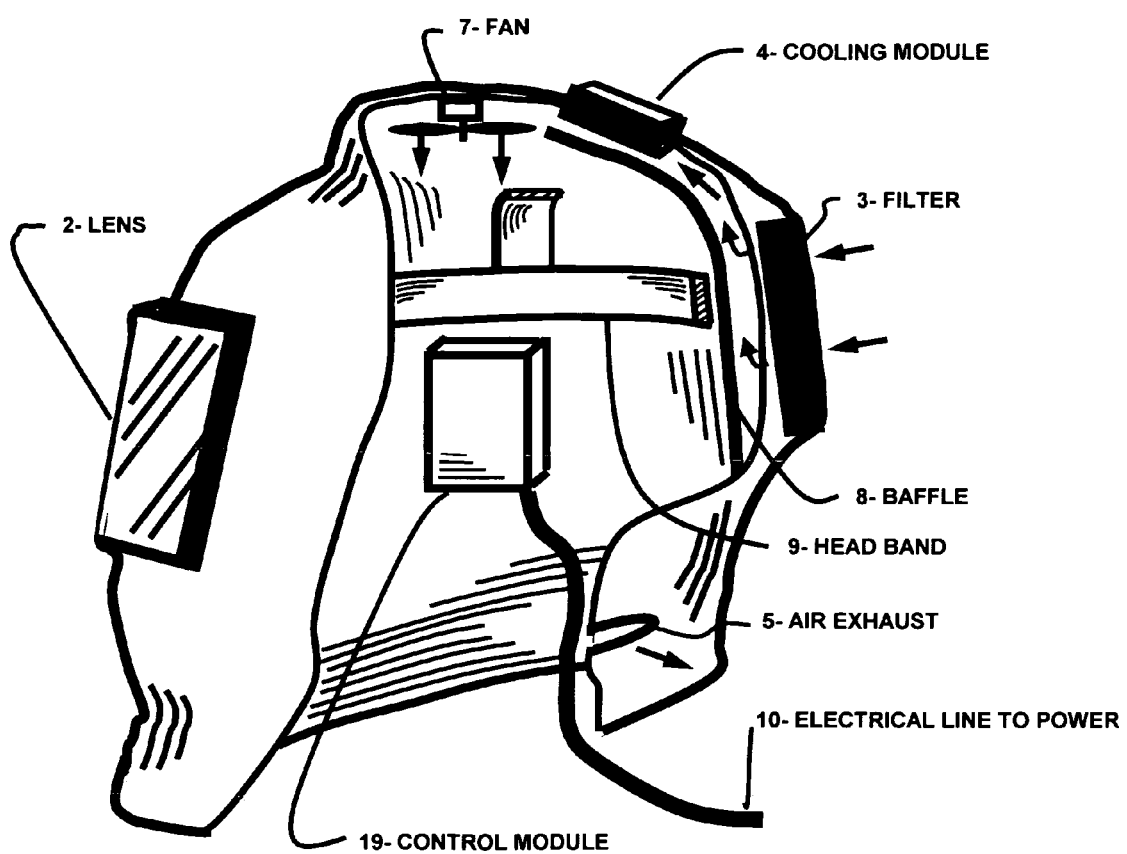
FIG. 6 is a cutaway view from the left side of the helmet showing the baffle, air passageway, thermal electric cooling module, electric motor driven fan, head band and electronic control module.

FIG. 6 shows helmet 1 viewed with a cutaway portion to show internal details. Filter 3 is shown above a baffle 8*a*. Baffle 8*a* is sealed to the inner top surface of the helmet 1 to provide an air passageway 8. Air passageway 8 directs the air coming through filter 3 to the fan 7. Fan 7 consists of an electric motor with fan blades. Air flow is shown with arrows. On the path to the fan 7 is located the cool side of the cooling module 4. The hot side of the cooling module 4 is exposed to the ambient air on the outside of helmet 1. Air passing over the cool side of cooling module 4 reduces its temperature. The cooled air is forced over the welders head and neck and exits through air exhaust 5. Control module 19 regulates and delivers power to the fan 7 and cooling module 4 through appropriate electrical connections. Depending on the auto-darkening lens 2 employed, it may be preferable to power and control darkening directly in lens 2 assembly and not through control module 19. A section of air exhaust 5 is visible in this view. A section of the head band 9 is show and can attach to helmet 1 in several ways. It can be connected as is typical in a hard hat device with appropriate fasteners to helmet 1 internal surface. If helmet 1 is made of the appropriate materials it may be able to replace the use of a hard hat. Power cord 10 is also shown.

Figure 7:
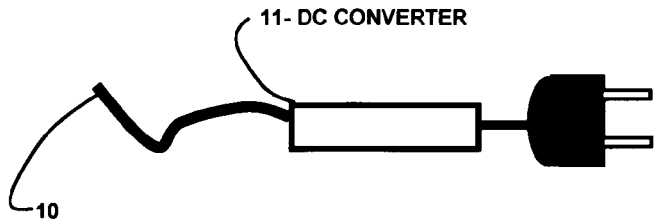
FIG. 7 shows schematically a way to power the helmet using an AC source with a DC converter.

FIG. 7 shows a way to power helmet 1 using an AC power source with a DC converter 11. The DC converter 11 produces low voltage DC power for welder safety. Voltage should be below 24 volts and possibly 12 volts. Power cord 10 can be connected directly to DC converter 11 using an appropriate plug connector.

Figure 8:
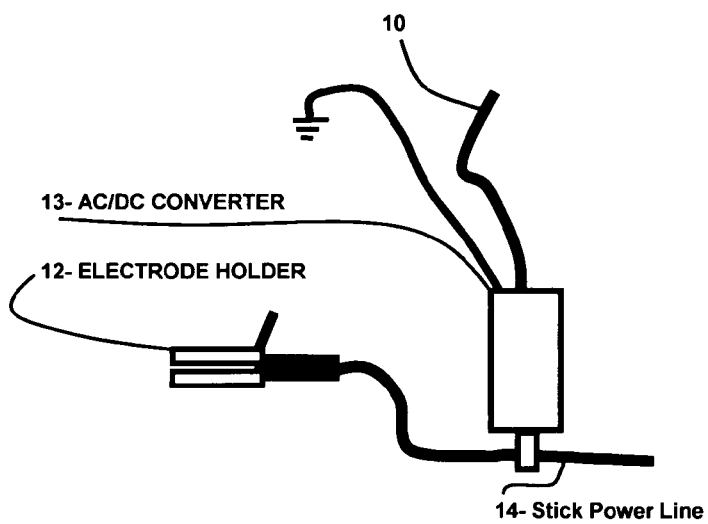
FIG. 8 shows schematically a way to power the helmet by converting AC/DC Stick welding power to low voltage DC.

FIG. 8 shows a way to power helmet 1 by connecting to AC/DC Stick welding power using AC/DC converter 13. AC/DC converter 13 converts the higher voltage power from a Stick welding power to a safer low voltage DC. If the Stick welding power is AC the AC/DC converter 13 changes the AC power to low voltage DC. The AC/DC converter 13 connects between the Stick electrode holder 12 and the Stick power line 14 coming from the Stick welding power supply. The AC/DC converter 13 also has a ground connection that the welder must attach to a good ground such as where the welding power ground is connected.

Figure 9:
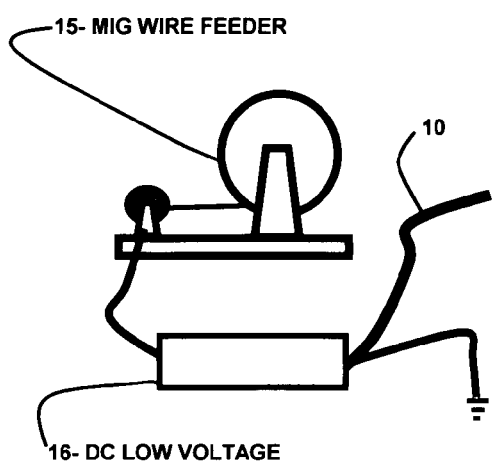
FIG. 9 shows schematically a way to power the helmet by connecting it to DC MIG welding power converting it to low voltage DC.

FIG. 9 shows a way to power helmet 1 by connecting to a MIG wire feeder using converter DC low voltage 16. Converter DC low voltage 16 produces a safer low DC voltage. DC low voltage 16 can be connected directly at the MIG wire feeder 15 where welding power is available. The converter DC low voltage 16 also has a ground connection that the welder must attach to a good ground such as where the welding power ground is connected. Power cord 10 connects directly to DC low voltage 16.

Figure 10:
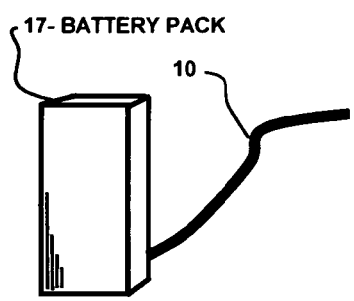
FIG. 10 shows schematically a way to power the helmet using a battery.

FIG. 10 shows helmet 1 powered using a battery pack 17. Battery pack 17 could be mounted in a back pack. It could utilize rechargeable batteries. Power cord 10 connects directly to battery pack 17.

Operation

Main Embodiment

Referring to FIG. 1. A welder places helmet 1 over their head having previously adjusted the head band 9 FIG. 6 for the proper fit. The welder than connects the power cord 10 that is attached to helmet 1 to an appropriate power source. Assuming power connection as shown in FIG. 7 is used, the fan 7 FIG. 6 will start and pull air through filter 3 into air passageway 8 FIG. 6. The resulting stream of air will pass the cool surface of cooling module 4 reducing the air temperature. Note that the cooling surface of cooling module 4 may contain cooling fins to increase the cool surface area. The welder will immediately receive cool, clean air that will be delivered over their head. The only requirement of the welder is to replace filter 3 periodically as it becomes clogged with welding fumes, metal dust from grinding etc.

Description and Operation

Additional Embodiments

Referring to FIG. 2. A welder adjusts the head band 9 FIG. 6 for the proper fit. The welder loosens the collar of their shirt or welding jacket if being worn. They then open the bottom of skirt 6 that has been attached to helmet 1. The attachment of the top of skirt 6 also seals to the bottom of helmet 1 preventing welding fumes from entering. Attachment and seal could be achieved, for example, with hook and loop fasteners. The welder than places skirt 6 and helmet 1 over their head and tucks the open end of skirt 6 under their shirt or welding jacket. The shirt or jacket is then buttoned or fastened by other means to capture the bottom of skirt 6. The welder than connects the power cord 10 that is attached to helmet 1 to an appropriate power source. Assume power connection as shown in FIG. 7 is being used, the fan 7 FIG. 6 will start and pull air through filter 3 into air passageway 8 FIG. 6. The resulting stream of air will pass the cool surface of cooling module 4 reducing the air temperature. Note that the cooling surface of cooling module 4 may contain cooling fins to increase the cool surface area. The welder will immediately receive cool, clean air that will be delivered over their head. The cooled clean air will exit the helmet 1 via the two openings, air exhaust 5 FIG. 5 and air exhaust 5a FIG. 5 at the bottom rear of helmet 1. Under some circumstances, such as when the environment has high levels of potentially toxic constituents, air exhaust 5 FIG. 5 and air exhaust 5a FIG. 5 could incorporate one way valves to prevent contaminated outside air from entering these openings. This could be accomplished with a device such as flexible rubber flap placed over the outside of openings air exhaust 5 FIG. 5 and air exhaust 5a FIG. 5. That option is not elaborated in this application. The only requirement of the welder is to replace filter 3 periodically as it becomes clogged with welding fumes, metal dust from grinding etc.

Referring to FIG. 4. The helmet 1 may contain optional temp knob 7 that allows the welder to adjust the degree of cooling. One way to operate temp knob 7 is with a shaft inserted through a small hole in the surface of helmet 1 directly into control module 19 FIG. 6. The adjustment could be regulated by control module 19 FIG. 6 as a percentage of available cooling from cooling module 4 or by a more elaborate system using temperature measuring and regulating the amount of cooling from cooling module 4. It is also possible to control the speed of the fan 7 FIG. 6 to control the degree of cooling. Another more elaborate control is achievable by controlling of fan 7 FIG. 6 in combination with degree of cooling from cooling module 4 using the appropriate algorithm incorporated in control module 19 FIG. 6.

Referring to FIG. 6. If the option of using temp knob 7 FIG. 4 is not employed, the fan 7 could operate at one speed and cooling module 4 and at maximum cooling. This could eliminate the need for control module 19 with the DC power from power cord 10 delivered directly to fan 7 and cooling module 4. Another possible control means if optional temp knob 7 FIG. 4 is not used is to regulate fan 7 speed and cooling module 4 cooling capacity with simple switches set by the welder prior to putting on the helmet 1.

Referring to FIG. 4. The helmet 1 may contain optional lens knob 8 that allows the welder to adjust the degree of darkening when a welding arc is present. One way to operate lens knob 8 is with a shaft inserted through a small hole in the surface of helmet 1 directly into control module 9 FIG. 6. The adjustment could regulate the degree of darkening of lens 2. Adjusting the amount of darkening of lens 2 can be done directly by control module 9 FIG. 6. Depending on the specific auto-darkening lens 2 utilized it may already contain a device to adjust the degree of darkening. This adjustment may be external or internal. It may be desirable to use that control device rather than incorporate this feature in control module 9 FIG. 6.

CONCLUSION, RAMIFICATION, AND SCOPE

This invention describes a welding helmet that encloses a welders head on five sides and with an optional skirt covers their neck. This helmet apparatus improves a welding operators working environment. It provides clean air that reduces welding fume levels in their breathing zone below the maximum suggested levels. It does this while improving the working environment for one of the most objectionable welding environmental issues, excess heat. By providing cool air to the welders head and neck area their whole body will feel cooler. Studies have shown cooling the head area reduces sweating in other parts of the body.

The fact that their overall environment and working conditions are improved will provide incentive for welding operators to use the helmet. The added advantage of having reduced burns in the head and neck area, especially when welding overhead is another benefit of this fully enclosed welding helmet.

The suggested use of an external power source provides the energy required to have a fan of sufficient capacity to draw air thorough a quality filter to capture potentially hazardous constituents of welding fumes. This externally supplied power allows the required cooling capacity thermal electric cooling modules to be used to significantly lower the ambient air temperature. This allows the welding operator to have sufficient cooling to improve their overall work environment.

The above description contains many specificities to provide illustrations of some of the embodiments. However it is understood that other obvious items might be added such as a mechanism that allows a portion of the helmet containing the auto-darkening lens to be lifted away from the helmet to provide access to outside air, valves to be placed over the air exhausts, helmet material selection and design that allow it to meet hard hat type requirements in addition to its welding functions. Thus the scope of the invention should be determined by the appended claims and their legal equivalents, rather than the examples given.

I claim:

1. A welding helmet apparatus that has an outer surface that encloses the front, right side, left side, top and back of the welding operators head and comprises:
   a) an auto-darkening lens located in the front portion of said helmet that when an electric arc is present changes from transparent to a dark shade providing adequate protection from the harmful effects of arc rays, and
   b) a headband to allow the helmet apparatus to be adjusted to fit different individuals, and
   c) an air filter to capture harmful particles of welding fume and prevent them from passing through said air filter, and
   d) an electric motor powered fan contained within said helmet apparatus, and
   e) an integral air passageway having a entry end and an exit end, and
   f) said air filter is located at said entry end of said air passageway, and
   g) said electric motor powered fan is located at said exit end of said air passageway, and
   h) a thermal electric cooling module is located in said air passageway such that the cooling surface of said cooling module is located in said passageway, and
   i) a heat-dissipating surface of said cooling module is located on the outside surface of said helmet apparatus, and
   j) said helmet obtaining power from an AC/DC power converter to keep voltage in said helmet below 24 volts, said AC/DC power converter connected to a ground source while obtaining welding power directly from either a MIG wire feeder at a point where welding power is available or from a stick electrode power line where welding power is available, said welding power obtaining power from a separate AC or DC welding power supply.

2. The helmet apparatus of claim 1 wherein said helmet apparatus includes a temp knob connected to an electronic control module to allow the welding operator to regulate the amount of cooling from said cooling module.

3. The helmet apparatus of claim 1, wherein a skirt is added to said helmet apparatus wherein said skirt is made of a flexible, fire resistant, low air permeability material and is of sufficient length to be placed under a shirt or jacket collar and attaches to the bottom of said helmet apparatus in such a manner as to seal said skirt to said helmet apparatus.

4. The helmet apparatus of claim 3, wherein said helmet apparatus includes air exhausts in said helmet apparatus to allow air to exit the helmet.

5. The helmet apparatus of claim 3, wherein said helmet apparatus includes a temp knob connected to an electronic control module to allow the welding operator to regulate the amount of cooling from said cooling module.

* * * * *